(12) United States Patent
Ishii

(10) Patent No.: US 8,449,557 B2
(45) Date of Patent: May 28, 2013

(54) VACUUM EXTRACTOR CUP FOR DELIVERY

(76) Inventor: Kenji Ishii, Saitama (JP)

( * ) Notice: Subject to any disclaimer, the term of this patent is extended or adjusted under 35 U.S.C. 154(b) by 0 days.

(21) Appl. No.: 13/127,351

(22) PCT Filed: Oct. 30, 2009

(86) PCT No.: PCT/JP2009/068646
§ 371 (c)(1),
(2), (4) Date: May 3, 2011

(87) PCT Pub. No.: WO2010/061710
PCT Pub. Date: Jun. 3, 2010

(65) Prior Publication Data
US 2011/0218547 A1    Sep. 8, 2011

(30) Foreign Application Priority Data
Nov. 27, 2008  (JP) .................. 2008-302364

(51) Int. Cl.
*A61B 17/42* (2006.01)
(52) U.S. Cl.
USPC ..................................... 606/123
(58) Field of Classification Search
USPC ............. 606/115, 119, 122, 123, 127, 128, 606/121
See application file for complete search history.

(56) References Cited

U.S. PATENT DOCUMENTS

| | | | |
|---|---|---|---|
| 2,702,038 A * | 2/1955 | Uddenberg et al. | 606/123 |
| 3,202,152 A * | 8/1965 | Wood et al. | 606/123 |
| 5,019,086 A * | 5/1991 | Neward | 606/123 |
| 5,693,058 A * | 12/1997 | Cavanagh et al. | 606/123 |
| 6,059,795 A * | 5/2000 | Wallace et al. | 606/123 |
| 6,506,166 B1 * | 1/2003 | Hendler et al. | 600/562 |
| 7,935,094 B2 * | 5/2011 | Lonky | 604/320 |

FOREIGN PATENT DOCUMENTS

| | | |
|---|---|---|
| CN | 201108482 Y | 9/2008 |
| JP | 03-009341 U | 1/1991 |
| JP | 3005948 U | 1/1995 |
| JP | 3064312 U | 1/2000 |
| JP | 2008-506490 A | 6/2008 |
| WO | 2010/061710 A1 | 1/2006 |

OTHER PUBLICATIONS

Translation of JP 03-009341 as received on Aug. 2, 2012.*
International Search Report dated Dec. 8, 2009 in corresponding International Application No. PCT/JP2009/068646.

* cited by examiner

*Primary Examiner* — Ryan Severson
*Assistant Examiner* — Jonathan W Miles
(74) *Attorney, Agent, or Firm* — The Law Office of Michael E. Kondoudis

(57) ABSTRACT

A vacuum extractor cup 2 for vacuum extractor delivery is provided which includes a cup portion 11 formed with a foldable and flexible material such as a sheet made of, for example, a vinyl material and in a cup-like shape with a sucking hole 13 on its bottom side and an extracting hole 14 on its opening side and includes a porous elastic member 12 formed with sponge. An extracting ring portion 16 has elastic force being larger than elastic force of a surrounding wall 15 in the cup portion 11. A convex/concave portion 17 is formed in an inner surface of the surrounding wall 15 in the cup portion 11 and the convex/concave portion 17 serves as a slipping-stop device between the cup portion 11 and porous elastic member 12.

8 Claims, 7 Drawing Sheets

VACUUM EXTRACTOR CUP FOR DELIVERY

FIELD OF THE INVENTION

The present invention relates to a vacuum extractor cup to be suitably used for extracting a fetal head when a fetus is delivered from a mother's body by vacuum-assisted delivery.

BACKGROUND OF THE INVENTION

Generally, a vacuum extractor to be used when a fetus is delivered from a mother's body by vacuum-assisted delivery has a vacuum extractor cup to be inserted into the mother's body to extract a fetal head from in the mother's body, an extracting handle connected with the vacuum extractor cup to extract the vacuum extractor cup together with the fetal head from the mother's body, an extracting tube connected to the extracting handle to apply negative pressure to the vacuum extractor cup through a communicating path formed in an inner portion of the extracting handle, a negative pressure applying pump to generate negative pressure, and a pressure reducing valve to limit the height of negative pressure.

As the vacuum extractor cup, a metal cup or a soft cap made of silicone has been conventionally used. In recent years, in some cases, a plastic cup, polyethylene cup, or the like is employed as the vacuum extractor cup.

Moreover, a product obtained by adding improvement to the general vacuum extractor is available (see Patent Reference 1).

Patent Reference 1: Japanese Patent Application Publication No. 2008-506490

BRIEF SUMMARY OF THE INVENTION

Incidentally, the maximum negative pressure to be applied to the vacuum extractor cup is regulated to be 80 kPa (60 cmHg, 0.82 kg/cm$^2$) by considering adverse effects on the fetal head. Therefore, in order to increase extracting force by the vacuum extractor while the negative pressure is being suppressed to the above maximum value or less, an increase in the extracting area of the vacuum extractor cup is required. However, the increase in the extracting area causes the increase in the size of the vacuum extractor cup. As a result, problems arise that, in the case of a metal cup, for example, the insertion of the metal cup into the mother's body becomes difficult and a risk of inducing the occurrence of injury to a vaginal wall of the mother's body increases.

In the case of a soft cup made of silicone, for example, the soft cup can be deformed to some extent when being inserted into the mother's body and, therefore, the insertion of the cup into the mother's body may be easily achieved when compared with the metal cup. However, another problem arises that the deformation of the soft cup at the time of extraction makes it difficult to maintain adhesiveness between the edge portion of the soft cup and the fetal head, resulting in the occurrence of slipping and coming out of the soft cup from the fetal head.

On the other hand, a conventional vacuum extractor cup using a shape preservation property (stiffness) material also has the problem that the fetal head swells and is deformed on the cup side due to negative pressure, as a result, causing the deformation (artificial caput succedaneum) of the fetal head to occur due to the application of negative pressure.

With respect to the above, a first object of the present invention is to provide a vacuum extractor cup for delivery which can be easily inserted into a mother's body and can provide sufficient extracting force and can reduce the occurrence of slipping and coming-out.

A second object of the present invention is to provide the vacuum extractor cup that can prevent the occurrence of artificial caput succedaneum.

In order to solve the above problems, a first aspect of the present invention is characterized in that the vacuum extractor cup for extracting a fetal head at time of delivery of a fetus includes a cup portion made of a foldable and flexible material and formed in a cup-like shape having a sucking hole, on its bottom side, to apply negative pressure, and an extracting hole, on its opening side, to extract a fetal head, and a porous elastic member formed in the cup portion.

By configuring as above, the cup portion can be easily inserted into the mother's body with the cup portion being folded, which enables the occurrence of injury to a vaginal wall of the mother's body to be prevented. Moreover, since the cup portion can be inserted into the mother's body while being folded, the size of the cup portion or extracting area can be increased. At the time of application of negative pressure, the porous elastic member formed in the cup portion adheres closely to the fetus head. This enables the area in which negative pressure is applied to the fetal head to be increased. Therefore, even if the negative pressure to be applied to the vacuum extractor cup is made lower compared with the conventional vacuum extractor cup, sufficient sucking and extracting force can be obtained, thus enabling the occurrence of slipping and coming-out of the vacuum extractor cup to be decreased and the occurrence of artificial caput succedaneum to be suppressed. Further, adherence of the soft cup portion and soft porous elastic member to the fetal head enables the occurrence of artificial caput succedaneum to be suppressed.

A second aspect of the present invention is characterized in that, in the above vacuum extractor cup, a surrounding wall in the cup portion is formed with a sheet made of a vinyl material.

By configuring as above, in the above vacuum extractor cup, by forming the surrounding wall of the cup portion with the sheet made of the vinyl material, it is made possible to form the soft cup portion having foldability and flexibility and to increase the effect of suppressing the occurrence of injury to a vaginal wall at the time of inserting the vacuum extraction cup and further to strengthen the sucking capability to the fetal head at the time of application of negative pressure.

A third aspect of the present invention is characterized in that, in the vacuum extractor cup, an extracting ring portion is formed in a surrounding edge of the sucking hole in the cup portion and the extracting portion has elastic force being larger than that of the surrounding wall of the vacuum extractor cup.

By configuring as above, the elastic force of the extracting ring portion in the vacuum extractor cup becomes restoring force to restore the cup portion from a folded state to its original cup-like state. Since the elastic force of the extracting ring portion is larger than that of the surrounding wall of the cup portion, the cup portion inserted into the mother's body in the folded state is restored reliably to its original cup state in the mother's body. Moreover, the extracting ring portion can adhere reliably to the fetal head at the time of application of negative pressure to prevent the leak of air. Especially, since the area in which negative pressure is directly applied to the fetal head by the porous elastic member is large, at the time of application of negative pressure, not only the extracting ring portion of the surrounding portion of the cup portion but also all of the surrounding wall of the cup portion and porous elastic member and extracting ring portion are directly attributable to the generation of sucking capability of the vacuum extractor cup to the fetal head. As a result, force applied at the time of extraction is not transmitted only to the surrounding edge of the cup portion in a concentrated manner and the force applied at the time of extraction concentrates on the surrounding portion of the cup portion edge and, therefore, the riding-up of the surrounding edge of the cup portion edge can be prevented.

A fourth aspect of the present invention is characterized in that, in the vacuum extractor cup of the third aspect, the extracting ring portion is made of gel-like rubber packing.

By configuring as above, it is made possible to obtain sufficient restoring force required to restore the cup portion from a folded state to its original cup-like state and to realize sufficient adhesiveness required to adhere the cup portion to the fetal head at the time of application of negative pressure.

A fifth aspect of the present invention is characterized in that, in the vacuum extractor cup of any one of the first to fourth aspects, a convex/concave portion is formed in an inner surface of the surrounding wall in the cup portion.

By configuring as above, negative pressure is applied in a state where the fetal head is struck to get into contact with the extracting hole of the cup portion, which causes the surrounding edge of the extracting hole to adhere closely to the fetal head and the cup portion is shrunk by negative pressure and the convex/concave portion formed in the inner surface of the surrounding wall of the cup portion adheres closely to the porous elastic member. Since the convex/concave portion adheres closely to the porous elastic member, the convex/concave portion serves as the slipping-stop device between the cup portion and the porous elastic member. This causes the integration between the cup portion and porous elastic member and enables the extracting force of the vacuum extractor cup to be stabilized.

A sixth aspect of the present invention is characterized in that, in the vacuum extractor cup of any one of the first to fourth aspects, the porous elastic member is made of sponge.

By configuring as above, the porous elastic member formed with sponge is easily deformed in a manner to match the shape of the fetal head, which provides excellent adhesiveness and sucking property. The porous elastic member gets into direct contact with the fetal head at the time of application of negative pressure and the adhering portion is made of the soft material such as sponge, which is much attributable to the suppression of the formation of artificial caput succedaneum.

A seventh aspect of the present invention is characterized in that, in the vacuum extractor cup of any one of the first to fourth aspects, the porous elastic member is formed in a circular plate-like shape.

By configuring as above, the porous elastic member is formed in a circular shape according to the shape of the inner side of the cup portion and, at the time of application of negative pressure, which allows the porous elastic member to be easily deformed in a manner to match the shape of the fetal head. This enables adhesiveness of the vacuum extractor cup to be increased.

According to the present invention, the insertion of the vacuum extractor cup into the mother's body is easy and sufficient extracting force can be obtained by the vacuum extractor cup and slipping and coming-out of the vacuum extractor cup can be prevented. The occurrence of artificial caput succedaneum can be suppressed.

DETAILED DESCRIPTION OF THE INVENTION

An embodiment of the present invention is described below by referring to drawings.

Figure 1:
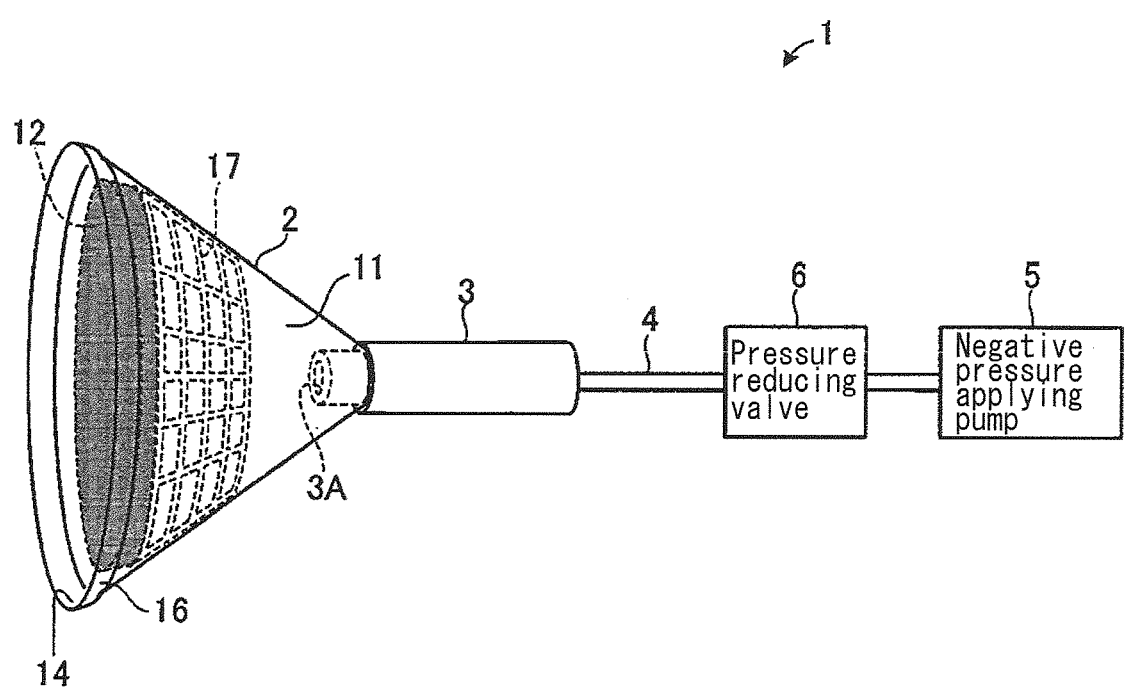
FIG. 1 is a diagram explaining a vacuum extractor having a vacuum extractor cup for delivery according to the embodiment of the present invention.

FIG. 1 is a diagram showing a vacuum extractor having a vacuum extractor cup for delivery of the embodiment of the present invention. The vacuum extractor 1 in FIG. 1 is an instrument for delivering a fetus from a mother's body by vacuum extractor delivery. The vacuum extractor 1 has a vacuum extractor cup 2 to extract the head of a fetus from the mother's body by inserting the cup 2 into the mother's body at time of extracting the fetus from the mother's body, an extracting handle 3 to extract the vacuum extractor cup 2 together with the fetal head from the mother's body, an extracting tube 4 to provide negative pressure to the vacuum extractor cup 2, a negative pressure applying pump 5 to generate negative pressure, and a pressure reducing valve 6 to limit the height of negative pressure. FIG. 1 shows the vacuum extractor cup 2 of the embodiment of the present invention.

One end side portion of the extracting handle 3 is connected to the vacuum extractor cup 2 and another end side portion of the extracting handle 3 is connected to one end side portion of the extracting tube 4. Another end side portion of the extracting tube 4 is connected through the pressure reducing valve 6 to the negative pressure applying pump 5. In an inner portion of the extracting handle 3, a communicating path 3A passing through in an axial direction is formed and the negative pressure generated by the negative pressure applying pump 5 is applied through the pressure reducing valve 6, extracting tube 4, and the communicating path 3A of the extracting handle 3 to the vacuum extractor cup 2.

Figure 2:
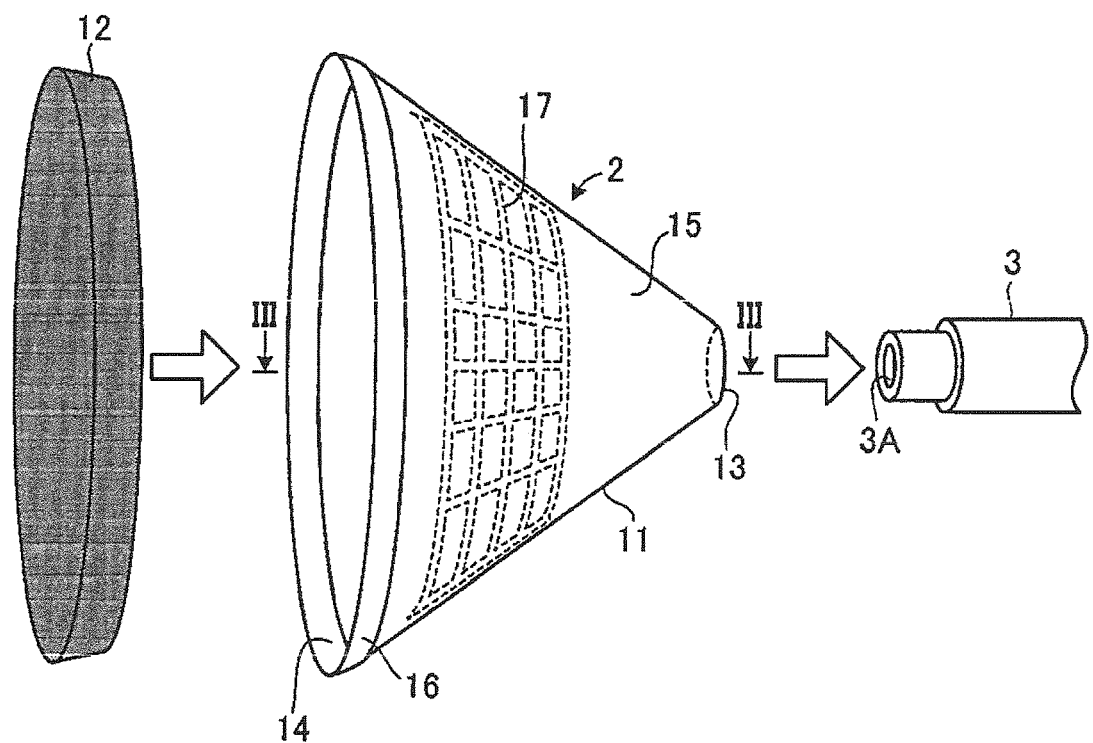
FIG. 2 is a perspective view showing a state in which the vacuum extractor cup is detached from an extracting handle and a cup portion of the vacuum extractor cup is separated from a porous elastic member.
Figure 3:
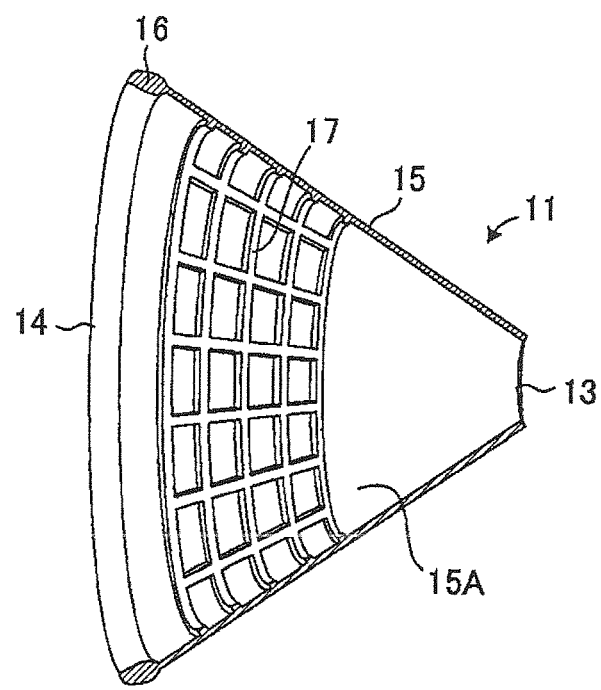
FIG. 3 is a cross-sectional view of the cup portion seen from the arrow III-III direction in FIG. 2.

FIG. 2 shows a state in which the vacuum extractor cup 2 is detached from the extracting handle 3 and the cup portion 11 of the vacuum extractor cup 2 is separated from a porous elastic member 12. FIG. 3 shows a cross section of the cup portion 11 seen from the arrow III-III direction in FIG. 2.

As shown in FIG. 2, the vacuum extractor cup 2 has the cup portion 11 and porous elastic member 12. The cup portion 11 is formed in a cup-like shape and a sucking hole 13 is formed on its bottom side and an extracting hole 14 is formed on its aperture side. The sucking hole 13 having a comparatively small diameter is used to insert an end portion of the extracting handle 3 when the vacuum extractor cup 2 and extracting handle 3 are coupled to each other and, at time of application of negative pressure, negative pressure is applied to the vacuum extractor cup 2 through the sucking hole 13. The extracting hole 14 has a comparatively large hole so as to fit the fetal head therein to suck the fetal head.

A surrounding wall 15 of the cup portion 11 other than a surrounding edge portion of the extracting hole 14 is made of a foldable and flexible material, more specifically a sheet made of a vinyl material. On the other hand, in the surrounding edge portion of the extracting hole 14, an extracting ring portion 16 is formed which is made of a foldable and flexible material having elastic force being larger than that of the surrounding wall 15, more specifically, of gel-like rubber packing. Moreover, as shown in FIG. 3, the thickness of the extracting ring portion 16 is larger than that of the surrounding wall 15 of the cup portion 11.

Further, as shown in FIG. 3, in the inner surface 15A of the surrounding wall 15 in the cup portion 11, a convex/concave portion 17 having a large number of convex and concave portions formed along all surrounding portions of the cup portion 11.

As shown in FIG. 2, the porous elastic member 12 is made of sponge and is formed in a circular plate shape. The porous elastic member 12, as shown in FIG. 1, is attached in the inner portion of the cup portion 11.

Figure 4:
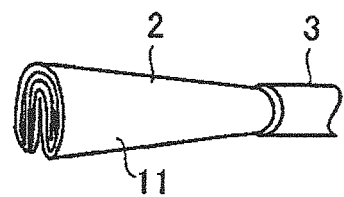
FIG. 4 is a perspective view showing a state in which the vacuum extractor cup is folded in quarto according to the embodiment of the present invention.
Figure 5:
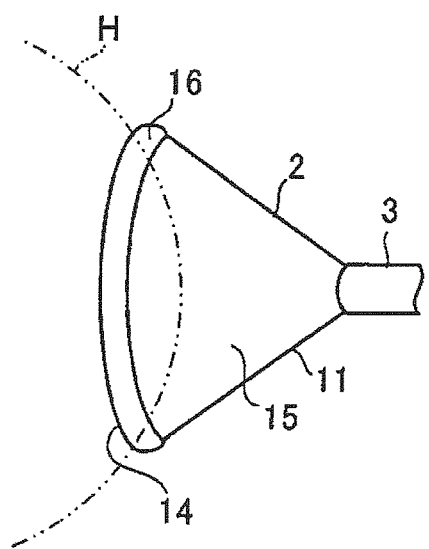
FIG. 5 is a perspective view showing a state in which the vacuum extractor cup is struck to get into contact with a fetal head according to the embodiment of the present invention.
Figure 6:
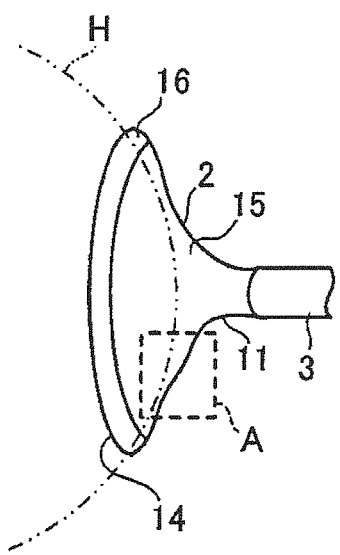
FIG. 6 is a perspective view showing a state in which negative pressure is applied to the vacuum extractor cup according to the present invention.

FIGS. 4 and 6 show the state of using the vacuum extractor cup 2 at the time of vacuum extractor delivery. As shown in FIG. 4, the vacuum extractor cup 2 is folded, for example, in quarto when being inserted into a mother' body through its vaginal opening. Since the cup portion 11 is made of the foldable and flexible material, the vacuum extractor cup 2 can be easily folded in quarto. Moreover, the porous elastic member 12 can be also folded together with the cup portion 11.

The vacuum extractor cup 2 inserted into the mother's body is restored therein to its original cup-like shape. The extracting ring portion 16 of the cup portion 11 has elastic force being larger than that of the surrounding wall 15 of the cup portion 11, which causes the cup portion 11 to be reliably restored to its original cup-like shape in the mother's body.

Then, the vacuum extractor cup 2 is struck to get into contact with the fetal head H so that part of the fetal head H in the mother's body fitly enters the inner portion of the extracting hole 14 and the negative pressure applying pump 5 is driven. This causes negative pressure to be applied in the vacuum extractor cup 2. When negative pressure is applied to the vacuum extractor cup 2, the extracting ring portion 16 of the cup portion 11 gets adhered closely to the fetal head H. Next, as shown in FIG. 6, the vacuum extractor cup 2 is shrunk by negative pressure and the porous elastic member 12 adheres closely to the fetal head H of a fetus. As a result, all of the extracting ring portion 16, surrounding wall 15, and porous elastic member 12 are attributable directly to the extraction of the fetal head H and extracting force of the vacuum extraction cup 2 to the fetal head H becomes power large enough to extract the fetal head H from the mother's body.

Figure 7:
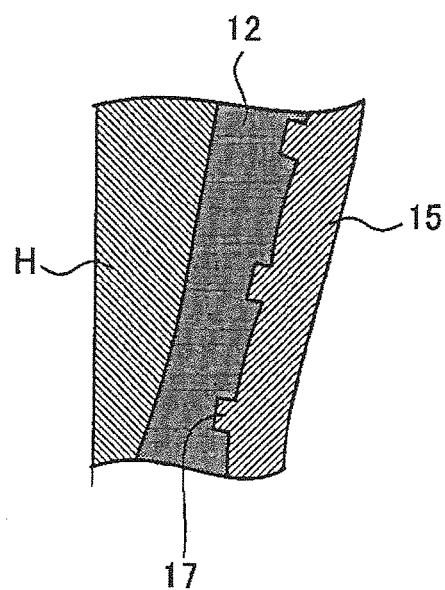
FIG. 7 is an enlarged cross sectional view showing the region A surrounded with the dashed line in FIG. 6.

FIG. 7 is an enlarged cross sectional view showing the region A surrounded with the dashed line in FIG. 6. As shown in FIG. 7, when the vacuum extractor cup 2 is shrunk and its porous elastic member 12 adheres closely to the fetal head H, a large number of convex and concave portions of the convex/concave portion 17 formed in the inner surface 15A of the surrounding wall 15 of the cup portion 11 encroach on the porous elastic member 12. This causes the porous elastic member 12 to be secured to the cup portion 11 and not to be moved therefrom. Thus, by the integration between the cup portion 11 and the porous elastic member 12, stabilized extracting force of the vacuum extractor cup 2 to the fetal head H can be generated.

When the extracting handle 3 is withdrawn in a state in which the vacuum extractor cup 2 is sucked to the fetal head H, the fetal head H can be extracted together with the vacuum extractor cup 2 from the mother's body.

As described above, according to the vacuum extractor cup 2 of the present invention, the vacuum extractor cup 2 is allowed to be inserted in a manner in which the cup portion 11 is folded, for example, in quarto and, therefore, the inserting of the vacuum extractor cup 2 can be easily achieved and the occurrence of injury to a vaginal wall can be suppressed at the time of the insertion of the vacuum extractor cup 2.

Moreover, the cup portion 11 can be inserted in a folded manner which allows the size of the cup portion 11 or its extracting area to be larger and the soft structure of the cup portion 11 allows the shape of the fetal head H to be easily deformable in a manner to match the shape of the fetal head H. Therefore, adhesiveness of the cup portion 11 to the fetal head H can be increased and the occurrence of slipping and coming out at time of extraction can be decreased.

Further, the porous elastic member 12 in the cup portion 11 adheres closely to the fetal head H at time of the application of negative pressure. This causes an increase in the area on which the negative pressure is applied directly to the fetal head H. As a result, even if the negative pressure to be applied to the vacuum extractor cup 2 is made low, the extracting force being large enough to extract the fetal head H can be generated. Since the negative pressure to be applied to the fetal head H can be lowered, the formation of artificial caput succedaneum in a fetus can be prevented.

Furthermore, the cup portion 11 is made of vinyl and the porous elastic member 12 is sponge, which means that both materials are soft. At time of the application of negative pressure, these soft materials get into contact with and adhered to the fetal head H and, therefore, swelling and deformation of the fetal head H toward the vacuum extractor head 2 can be prevented. This enables the formation of artificial caput succedaneum in the fetus to be prevented.

By elastic force of the extracting ring portion 16 formed in the cup portion 11, the vacuum extractor cup 2 after having been folded and inserted into the mother's body can be reliably restored to its original shape and the fetal head H can be firmly fitted into the extracting hole 14. Moreover, at time of the application of negative pressure, by using the extracting ring portion 16, the cup portion 11 can be reliably adhered closely to the fetal head H. Since all of the extracting ring portion 16, surrounding wall 15 of the cup portion 11, and porous elastic member 12 can be directly attributable to the generation of sucking capability of the vacuum extractor cup 2 to the fetal head, concentrated transmission of the force for extraction to only surrounding portions of the cup portion 11 can be avoided and, therefore, the riding-up of the surrounding portions of the cup portion 11 caused by the concentration of force at time of the extraction can be prevented.

By the convex/concave portion 17 formed in the inner surface 15A of the surrounding wall 15 of the cup portion 11, at time of the application of negative force, the porous elastic member 12 can be integrally coupled to the cup portion 11 and the sucking force of the vacuum extractor cup 2 to the fetal head H can be stabilized.

Additionally, in the above embodiment, the example is described in which the surrounding wall 15 of the cup portion 11 is formed with a sheet made of a vinyl material, however, the present invention is not limited to this. That is, the surrounding wall 15 may be made of other foldable and flexible materials such as nylon, polyethylene, laminated film, silicon, or the like.

In the above embodiment, the example is described in which the extracting ring portion 16 of the cup portion 11 is made of gel-like rubber packing, however, the present invention is not limited to this. That is, the extracting ring portion 16 may be made of silicon, plastic elastomers, metal, or the like. Moreover, the extracting ring portion 16 and the surrounding wall 15 may be made of the same material. In this case, by making the thickness of the extracting ring portion 16 be larger than that of the surrounding wall 15, the elastic force of the extracting ring portion 16 can be made larger than that of the surrounding wall 15.

The shape of the convex/concave portion 17 formed in the inner surface 15A of the surrounding wall 15 of the cup portion 11 is not limited to the shape shown in FIG. 3. For example, in the inner surface 15A of the surrounding wall 15, a circular or spiral protruded bar may be formed or a large number of cylindrical protrusions each having a small diameter may be arranged.

In addition, the material of the porous elastic member 12 is not limited to sponge and filters of various kinds, urethane foam, glass wool, or the like may be used as its material. The shape of the porous elastic member 12 is not limited to a circular plate. For example, the porous elastic member 12 may be cup-shaped or cone-shaped and be smaller in size than the cup portion 11.

Figure 8:
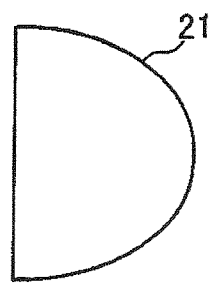
FIG. 8 is a diagram explaining another shape of the cup portion having a cup shape.
Figure 9:
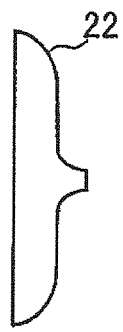
FIG. 9 is a diagram explaining further another shape of the cup portion having the cup shape.
Figure 10:
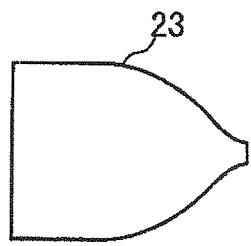
FIG. 10 is a diagram explaining further another shape of the cup portion having the cup shape.

The cup portion 11 of the present invention is cup-shaped. The cup portion 11 shown in FIGS. 1 and 3 has an approximately cone-like shape being hollow and bottomless. The cup portion 21 shown in FIG. 8 has a teacup-like shape. The cup portion 22 shown in FIG. 9 has a dish-like shape. The cup portion 23 shown in FIG. 10 has a glass-like shape.

It is understood that the present invention is not limited to the above embodiment and may be appropriately changed or modified without departing from the scope and spirit that can be read from the Claims and the entire Specifications and the vacuum extractor cup for delivery accompanied by such modifications are also encompassed in the technological thought of the present invention.

Explanation of Reference Symbols

1: Vacuum extractor
2: Vacuum extractor cup
11: Cup portion
12: Porous elastic member
13: Sucking hole
14: Extracting hole
15: Surrounding wall
16: Extracting ring portion
17: Convex/concave portion

What is claimed is:

1. A vacuum extractor cup for extracting a fetal head at time of delivery of a fetus comprising:
   a cup portion made of a foldable and flexible material and formed in a cup-like shape having a sucking hole, on its bottom side, to apply negative pressure, and an extracting hole, on its opening side, to suck a fetal head; and
   a porous elastic member formed in the cup portion,
   wherein the cup portion is constructed so that its entire part may adhere closely to the fetal head, when the cup portion is shrunk at time of application of negative pressure, through the porous elastic member.

2. The vacuum extractor cup according to claim 1, wherein a surrounding wall in the cup portion is formed with a sheet made of a vinyl material.

3. The vacuum extractor cup according to claim 1, wherein an extracting ring portion is formed in a surrounding edge of the sucking hole in the cup portion and the extracting portion has elastic force being larger than elastic force of the surrounding wall of the vacuum extractor cup.

4. The vacuum extractor cup according to claim 3, wherein the extracting ring portion is made of gel-like rubber packing.

5. The vacuum extractor cup according to claim 1, wherein a convex/concave portion is formed in an inner surface of the surrounding wall in the cup portion.

6. The vacuum extractor cup according to claim 1, wherein the porous elastic member is made of sponge.

7. The vacuum extractor cup according to claim 1, wherein the porous elastic member is formed in a circular plate-like shape.

8. A vacuum extractor cup for extracting a fetal head at time of delivery of a fetus comprising:
   a cup portion made of a foldable and flexible material and formed in a cup-like shape having a sucking hole, on its bottom side, to apply negative pressure, and an extracting hole, on its opening side, to suck a fetal head; and
   a porous elastic member formed in the cup portion,
   wherein the cup portion is dimensioned and configured so that only a portion thereof adheres closely to the fetal head through the porous elastic member, when the cup portion is shrunk at time of an application of negative pressure.

* * * * *